(12) United States Patent
Leone (10) Patent No.: US 6,780,167 B2
(45) Date of Patent: Aug. 24, 2004

(54) MULTI-LUMEN INTRAVENOUS EXTENSION AND METHOD FOR CONVEYING MEDICINAL FLUIDS

(76) Inventor: James Ernest Leone, 5865 SW. 108th St., Pinecrest, FL (US) 33156

(*) Notice: Subject to any disclaimer, the term of this patent is extended or adjusted under 35 U.S.C. 154(b) by 12 days.

(21) Appl. No.: 10/373,898

(22) Filed: Feb. 25, 2003

(65) Prior Publication Data

US 2003/0130617 A1 Jul. 10, 2003

Related U.S. Application Data

(63) Continuation-in-part of application No. 09/561,229, filed on Apr. 28, 2000, now abandoned.

(51) Int. Cl.$^7$ .............................................. A61M 37/00
(52) U.S. Cl. ........................... 604/82; 604/27; 604/246; 604/173; 604/523
(58) Field of Search ............................... 604/27, 36, 39, 604/43, 40, 80, 81, 82, 83, 93.01, 173, 181, 264, 523, 246–249; 285/120.1, 124.1

(56) References Cited

U.S. PATENT DOCUMENTS

| | | | |
|---|---|---|---|
| 2,286,462 A | | 6/1942 | Chaffin |
| 4,072,146 A | | 2/1978 | Howes |
| 4,346,703 A | * | 8/1982 | Dennehey et al. .......... 604/406 |
| 4,585,435 A | | 4/1986 | Vaillancourt |
| 4,601,697 A | | 7/1986 | Mammolenti et al. |
| 4,908,018 A | | 3/1990 | Thomsen |
| 4,968,307 A | | 11/1990 | Dake et al. |
| 4,994,048 A | | 2/1991 | Metzger |
| 5,041,083 A | | 8/1991 | Tsuchida et al. |
| 5,190,525 A | | 3/1993 | Oswald et al. |
| 5,211,627 A | * | 5/1993 | William ....................... 604/82 |
| 5,279,587 A | | 1/1994 | Weenig |
| 5,364,377 A | | 11/1994 | O'Neil |
| 5,676,659 A | * | 10/1997 | McGurk ..................... 604/527 |
| 5,713,853 A | * | 2/1998 | Clark et al. ................ 604/509 |
| 5,833,652 A | | 11/1998 | Preissman et al. |
| 5,967,569 A | | 10/1999 | Vaillancourt et al. |
| 6,030,371 A | | 2/2000 | Pursley |
| 6,139,539 A | * | 10/2000 | Baudino ..................... 604/537 |

OTHER PUBLICATIONS

Hunsaker et al.: "Engineering Applications of Fluid Mechanics" McGraw–Hill Book Company, Inc. New York and London, 1947.

* cited by examiner

Primary Examiner—LoAn H. Thanh
Assistant Examiner—Jennifer Maynard
(74) Attorney, Agent, or Firm—Laurence A. Greenberg; Werner H. Stemer; Gregory L. Mayback (57) ABSTRACT

The multi-lumen intravenous extension system and method for independently conveying medicinal fluids include an extension including an elongate cylindrical body having a main lumen extending axially therein and at least one satellite lumen extending parallel with the main lumen in the extension, a coupling/connector at a proximal end of the extension, a liquid supply system connected to the proximal end connector for delivering liquid to the main lumen, at least one syringe coupled to the proximal connector for supplying a drug medication, pharmaceutical agent, or other liquid to the satellite or secondary lumen, and a connector forming a mixing chamber coupled to a distal end of the extension. The connector is adapted for connection to an intravenous or intra-vascular catheter or needle leading to an intra-vascular access site. The fluidic connection between the mixing connector and the multi-lumens of the extension substantially prevents over-pressurization of the vascular access device.

31 Claims, 4 Drawing Sheets

MULTI-LUMEN INTRAVENOUS EXTENSION AND METHOD FOR CONVEYING MEDICINAL FLUIDS

CROSS-REFERENCE TO RELATED APPLICATION

This application is a continuation-in-part of application Ser. No. 09/561,229, filed Apr. 28, 2000 now abandoned.

BACKGROUND OF THE INVENTION

1. Field of the Invention

The present invention relates to a multi-lumen intravenous extension for transmitting liquids to a position adjacent a body and for mixing the fluids as close as possible to the point where they are injected into the blood stream of the body. For such a purpose, the multi-lumen intravenous extension of the present invention includes at least two, and possibly up to five, lumens, namely a main lumen for a carrier fluid, such as a saline solution, and at least one, and up to four, satellite lumens for carrying medication(s) to the body and mixing the medication(s) as close as possible to the point of input into the blood stream of the body at a proximal end of an intravenous catheter.

2. Description of the Prior Art

Heretofore catheters have been proposed for mixing components in the catheter prior to delivery of the mixture to a human body. Examples of analogous and non-analogous catheters are disclosed in the following analogous and non-analogous U.S. patents:

| U.S. Pat. No. | Patentee |
| --- | --- |
| 4,585,435 | Vaillancourt |
| 4,908,018 | Thomsen |
| 4,968,307 | Dake et al. |
| 5,041,083 | Tsuchida et al. |
| 5,190,525 | Oswald et al. |
| 5,279,587 | Weenig |
| 5,364,377 | O'Neil |
| 5,833,652 | Pressman et al. |
| 6,030,371 | Pursley |

Thomsen and the Oswald et al. both disclose manifolds for injecting drugs, medications or liquids into an intravenous catheter or conduit.

Dake et al. disclose a catheter having a central lumen for receiving a guide wire and four satellite lumens that extend coaxially with the central lumen. The outer periphery of the catheter has openings that communicate, respectively, with the four different satellite lumens for enabling four different fluids to be introduced into the vessel in which the catheter is inserted.

Pressman et al. disclose a component mixing catheter including an inner tubular body having a central lumen for a main fluid and an outer tubular body with an annular space between the inner tubular body and the outer tubular body for receiving a second liquid and the wall of the inner tubular body having holes therethrough for introducing the second liquid from the annular space into the main lumen where the second liquid is combined with the main fluid.

Vaillancourt shows, in FIG. 8, a septated or partitioned internal lumen where a micro-bore lumen and septal wall 51 are co-extruded within the internal diameter or circumference of the outer tube 52 such that both the diameter of the micro-bore lumen and septal wall extend inward and protrude into the circumference defining the lumen of the outer tube 52. In other words, the intraluminal position of the micro-bore lumen and septal wall 51 reduces the cross-sectional area of the fluid conveying lumen of the outer tube 52. This intraluminal configuration is consistent with the other embodiments of the Vaillancourt patent because Vaillancourt describes that the satellite tubes and lumen are contained within the lumen of the outer tube 52. In Vaillancourt, all disclosed embodiments reduce the cross-sectional area of the outer tube 52.

Weenig discloses a self-clearing extension set for delivery of fluid to a patient. FIG. 2 of Weenig discloses a dual lumen extension tube 90 that is virtually identical to FIG. 8 of Vaillancourt. Just like in Vaillancourt, Weenig discloses a small lumen 156 and separating membrane 158 extending inward and protruding into the circumference defining the large lumen 154. In other words, the intraluminal position of the small lumen 156 and wall 158 reduces the cross-sectional area of the fluid conveying large lumen 154.

Flow in a tube is described by the Hagen-Poiseuille Law, which provides that flow is linearly proportional to pressure of the fluid in the tube, viscosity of the fluid, and length of the tube, but is exponentially proportional to the radius of the tube. See Engineering Applications of Fluid Mechanics, J. C. Hunsaker and B. G. Rightmire, McGraw-Hill Book Company, Inc., 1947, indicating the principles of the Hagen-Poiseuille Law. Specifically, the Hagen-Poiseuille Law is described by the formula:

$$Q = \frac{\pi r^4 (P_1 - P_2)}{8 \mu L}$$

where:

Q is flow rate through a tube;

r is the radius of the tube;

$\mu$ is the viscosity of the fluid;

L is the length of the tube; and

P is the pressure of the fluid.

Therefore, for a small decrease in the radius of the tube, a substantial reduction in flow ensues.

For the tubular embodiments described in Vaillancourt, i.e., for an inner tube 51 having an interior diameter of 0.020 inches, the micro-bore tube 51 occupies a significant amount of space and flow rate through Vaillancourt's outer tube 51 is affected to a substantial degree when viewed in terms of delivering a medication to a patient. Contrast Vaillancourt at col. 6, lines 56 to 60. Specifically, the embodiment shown in FIG. 8 of Vaillancourt, which is partially within the wall of outer tube 52, decreases flow in outer tube 52 by at least 18 percent. If a tube such as inner tube 51 is inserted entirely within outer tube 52 as illustrated in FIGS. 6, 7, 9, and 10 of Vaillancourt, then flow is decreased by at least 28 percent. If the embodiment of Vaillancourt was changed to place two inner tubes 51 within outer tube 52, then flow in outer tube 52 is decreased by at least 54 percent.

Similarly, for the tubular embodiment described in Weenig, small lumen 156 occupies a significant amount of space and flow rate through Weenig's large lumen 145 and is affected to a substantial degree when viewed in terms of delivering a medication to a patient.

Specifically, the embodiment shown in FIG. 2 of Weenig, having the small lumen 156 partially within the large lumen 154, decreases flow in large lumen 154 by approximately 15 to 20 percent.

Such a decrease in flow within the Vaillancourt outer tube 52 or the Weenig large lumen 154 is entirely undesirable.

The purpose of fluid conveyed in the lumen of outer tube 52 is for patient fluid maintenance and volume fluid bolus, both of which may require delivering a large volume of fluid in a short period of time. Compromising the ability to rapidly convey a large volume of fluid could have detrimental effects on the patient.

O'Neil discloses three or four entirely separate lumens that are each glued/fastened into a common connector 42. See O'Neil at FIGS. 6 and 8. In each multi-lumen embodiment, the largest lumen 4 is compressed and, therefore, obstructed.

Tsuchida discloses a multi-lumen catheter. This catheter is shown in FIG. 1b. As set forth therein, each of the lumen are triangular in shape.

Finally, Pursley discloses a system for manufacturing catheters. However, Pursley is expressly distinguished from extrusion processes.

SUMMARY OF THE INVENTION

It is accordingly an object of the invention to provide a multi-lumen intravenous extension and method for conveying medicinal fluids that overcome the hereinafore-mentioned disadvantages of the heretofore-known devices and methods of this general type and that are configured to integrate with existing standardized infusion systems. The multi-lumen intravenous extension is positioned between an intra-vascular or intravenous access site and an infusion system typically including a supply of saline and syringes for injecting drugs, medications or other liquids into the multi-lumen intravenous extension. The multi-lumen intravenous extension allows for organized and efficient delivery and administration of a wide variety of medications and pharmaceutical agents, using less priming volume, minimizing effects of carrier fluid rates, and requiring only a minimal amount of medication mixing.

With the foregoing and other objects in view, in a drug delivery system having a medicinal fluid supply system with at least two supplies independently supplying at least two medicinal fluids at a distal connector, there is provided, in accordance with the invention, an extension including a mixing connector defining a mixing chamber to be fluidically connected to a vascular access device for simultaneously supplying the at least two medicinal fluids to a patient, and an intramural extrusion tube for conveying the at least two medicinal fluids independent from one another, the tube having a proximal end capable of being connected to the distal connector, a distal end connected to the mixing connector, a single, substantially ring-shaped tubular wall having a wall inner circumference and a wall outer circumference, the wall defining at least two channels including a substantially circular primary channel for conveying a first of the medicinal fluids, the primary channel having a primary channel outer circumference defined by the wall inner circumference, a proximal opening capable of being fluidically connected to a first of the supplies to supply the first medicinal fluid to the primary channel, and a distal opening fluidically connected to the mixing chamber for substantially preventing over-pressurization of the vascular access device, and a substantially circular secondary channel for conveying a second of the medicinal fluids, the secondary channel entirely disposed between the wall inner circumference and the wall outer circumference and having a proximal opening capable of being fluidically connected to a second of the supplies to supply the second medicinal fluid to the secondary channel and a distal opening fluidically connected to the mixing chamber for substantially preventing over-pressurization of the vascular access device.

With the objects of the invention in view, there is also provided a drug delivery system, including a medicinal fluid supply system having a distal connector and at least two supplies independently supplying at least two medicinal fluids at the distal connector, a mixing connector defining a mixing chamber, an intramural extrusion tube for conveying the at least two medicinal fluids independent from one another, the tube having a proximal end connected to the distal connector, a distal end connected to the mixing connector, a single, substantially ring-shaped tubular wall having a wall inner circumference and a wall outer circumference, the wall defining at least two channels including a substantially circular primary channel for conveying a first of the medicinal fluids, the primary channel having a primary channel outer circumference defined by the wall inner circumference, a proximal opening fluidically connected to a first of the supplies to supply the first medicinal fluid to the primary channel, and a distal opening fluidically connected to the mixing chamber, a substantially circular secondary channel for conveying a second of the medicinal fluids, the secondary channel entirely disposed between the wall inner circumference and the wall outer circumference and having a proximal opening fluidically connected to a second of the supplies to supply the second medicinal fluid to the secondary channel and a distal opening fluidically connected to the mixing chamber, and a vascular access device fluidically connected to the mixing chamber for simultaneously supplying the at least two medicinal fluids to a patient, the distal opening of the primary channel and the distal opening of the secondary channel substantially preventing over-pressurization of the vascular access device.

With the objects of the invention in view, in combination with a drug delivery system having a medicinal fluid supply system having a distal connector and at least two supplies independently supplying at least two medicinal fluids at the distal connector, a mixing connector defining a mixing chamber, and a vascular access device fluidically connected to the mixing chamber for simultaneously supplying the at least two medicinal fluids to a patient, there is also provided an extension including an intramural extrusion tube for conveying the at least two medicinal fluids independent from one another, the tube having a proximal end connected to the distal connector, a distal end connected to the mixing connector, a single, substantially ring-shaped tubular wall having a wall inner circumference and a wall outer circumference, the wall defining at least two channels including a substantially circular primary channel for conveying a first of the medicinal fluids, the primary channel having a primary channel outer circumference defined by the wall inner circumference, a proximal opening fluidically connected to a first of the supplies to supply the first medicinal fluid to the primary channel, and a distal opening fluidically connected to the mixing chamber for substantially preventing over-pressurization of the vascular access device, and a substantially circular secondary channel for conveying a second of the medicinal fluids, the secondary channel entirely disposed between the wall inner circumference and the wall outer circumference and having a proximal opening fluidically connected to a second of the supplies to supply the second medicinal fluid to the secondary channel and a distal opening fluidically connected to the mixing chamber for substantially preventing over-pressurization of the vascular access device.

With the objects of the invention in view, there is also provided a drug delivery extension, including a mixing connector defining a mixing chamber to be fluidically connected to a vascular access device for simultaneously supplying at least two medicinal fluids to a patient and an intramural extrusion tube for conveying the at least two fluids independent from one another, the tube having a proximal end, a distal end, a single, substantially ring-shaped tubular wall having a wall inner circumference and a wall outer circumference, the wall defining at least two channels including a substantially circular primary channel for conveying a first fluid, the primary channel having a primary channel outer circumference defined by the wall inner circumference and first and second openings respectively opening at the proximal end and the distal end, and a substantially circular secondary channel for conveying a second fluid, the secondary channel entirely disposed between the wall inner circumference and the wall outer circumference and having first and second openings respectively opening at the proximal end and the distal end, the second opening of the primary channel and the second opening of the secondary channel fluidically connected to the mixing chamber and substantially preventing over-pressurization of the vascular access device.

In accordance with another feature of the invention, the mixing connector is a male Luer lock connector. The mixing connector has a size equal to the medical industry standard for insertion into a vascular access device. The term "standard," as it is used herein, relates to the industry standard corresponding to ISO 594-1:1986.

In accordance with a further feature of the invention, the vascular access device is a catheter.

In accordance with an added feature of the invention, the intramural extrusion tube conveys at least three medicinal fluids independent from one another, the wall defines at least three channels including a substantially circular second secondary channel for conveying a third of the medicinal fluids, and the second secondary channel is entirely disposed between the wall inner circumference and the wall outer circumference and has a proximal opening capable of being fluidically connected to a third of the supplies to supply the third medicinal fluid to the second secondary channel and a distal opening fluidically connected to the mixing chamber for substantially preventing over-pressurization of the vascular access device.

In accordance with an additional feature of the invention, the secondary channel has an outer circumference, the second secondary channel has an outer circumference, and the primary channel outer circumference is entirely outside the outer circumferences of the first and second secondary channels or each of the primary channel outer circumference, the outer circumference of the secondary channel, and the outer circumferences of second secondary channel are entirely separate from one another.

In accordance with yet another feature of the invention, the first opening at the proximal end of the secondary channel is to be fluidically connected to a first syringe, the first opening at the proximal end of the second secondary channel is to be fluidically connected to a second syringe, and/or the first opening at the proximal end of the primary channel is to be fluidically connected to a bag of saline.

In accordance with yet a further feature of the invention, the primary channel has an internal diameter at least as large as the medical industry standard for infusion tubing. In particular, the primary channel has an internal diameter of approximately 0.122 inches.

In accordance with yet an added feature of the invention, the second channel has no decreasing effect on the internal diameter of the primary channel and/or each of the second channel and the second secondary channel have no decreasing effect on the internal diameter of the primary channel.

In accordance with yet an additional feature of the invention, the tube has a length and the primary channel and each secondary channel extend through an entirety of the length.

In accordance with again another feature of the invention, each of the secondary channel and the second secondary channel has an internal diameter between 0.030 and 0.050 inches.

In accordance with again a further feature of the invention, the wall defines a substantially circular third secondary channel for conveying a fourth fluid and the third secondary channel is entirely disposed between the wall inner circumference and the wall outer circumference and has first and second openings respectively opening at the proximal end and the distal end, the second opening of the third secondary channel is fluidically connected to the mixing chamber and substantially prevents over-pressurization of the vascular access device.

In accordance with again an added feature of the invention, the wall defines a substantially circular fourth secondary channel for conveying a fifth fluid and the fourth secondary channel is entirely disposed between the wall inner circumference and the wall outer circumference and has first and second openings respectively opening at the proximal end and the distal end, the second opening of the fourth secondary channel is fluidically connected to the mixing chamber and substantially prevents over-pressurization of the vascular access device.

In accordance with again an additional feature of the invention, the wall defines a substantially circular fifth secondary channel for conveying a sixth fluid and the fifth secondary channel is entirely disposed between the wall inner circumference and the wall outer circumference and has first and second openings respectively opening at the proximal end and the distal end, the second opening of the fifth secondary channel is fluidically connected to the mixing chamber and substantially prevents over-pressurization of the vascular access device.

With the objects of the invention in view, there is also provided a method for conveying at least two medicinal fluids independent from one another, which includes the steps of providing a mixing connector defining a mixing chamber to be fluidically connected to a vascular access device for simultaneously supplying the at least two medicinal fluids to a patient, co-extruding a single, substantially ring-shaped tubular wall having a wall inner circumference, a wall outer circumference, a proximal end, and a distal end, the wall defining at least two channels including a substantially circular primary channel for conveying a first of the fluids, the primary channel having a primary channel outer circumference defined by the wall inner circumference and first and second openings respectively opening at the proximal end and the distal end, and a substantially circular secondary channel for conveying a second of the fluids, the secondary channel being entirely disposed between the wall inner circumference and the wall outer circumference and having first and second openings respectively opening at the proximal end and the distal end, and fluidically connecting the second opening of the primary channel and the second opening of the secondary channel to the mixing chamber and, thereby, substantially prevent over-pressurization of the vascular access device.

In accordance with still another mode of the invention, there are also provided the steps of co-extruding the wall with a substantially circular second secondary channel for conveying a third of the fluids, the second secondary channel being entirely disposed between the wall inner circumference and the wall outer circumference and having first and second openings respectively opening at the proximal end and the distal end and fluidically connecting the second opening of the second secondary channel to the mixing chamber and, thereby, substantially prevent over-pressurization of the vascular access device.

With the objects of the invention in view, there is also provided a method for delivering at least two medicinal fluids, which includes the steps of providing a medicinal fluid supply system having a distal connector and at least two supplies independently supplying at least two medicinal fluids at the distal connector, providing a mixing connector having an inlet and an outlet and defining a mixing chamber fluidically connected to the inlet and the outlet, co-extruding a single, substantially ring-shaped tubular wall having a wall inner circumference, a wall outer circumference, a proximal end, and a distal end, the wall defining at least two channels including a substantially circular primary channel for conveying a first of the fluids, the primary channel having a primary channel outer circumference defined by the wall inner circumference, a proximal opening, and a distal opening, a substantially circular secondary channel for conveying a second of the fluids, the secondary channel entirely disposed between the wall inner circumference and the wall outer circumference and having a proximal opening and a second opening, and connecting the proximal end of the wall to the distal connector to fluidically connect the proximal opening of the primary channel to a first of the supplies to supply the first fluid to the primary channel and fluidically connect the proximal opening of the secondary channel to a second of the supplies to supply the second fluid to the secondary channel, connecting the distal end of the wall to the inlet of the mixing connector to fluidically connect the distal opening of the primary channel to the input of the mixing chamber, fluidically connect the second opening of the secondary channel to the input of the mixing chamber, and fluidically connecting a vascular access device to the outlet of the mixing chamber for simultaneously supplying the at least two medicinal fluids to a patient, the distal opening of the primary channel and the second opening of the secondary channel substantially preventing over-pressurization of the vascular access device.

With the objects of the invention in view, there is also provided a method for delivering at least three medicinal fluids, which includes the steps of providing a medicinal fluid supply system having a distal connector and at least three supplies independently supplying at least three medicinal fluids at the distal connector, providing a mixing connector having an inlet and an outlet and defining a mixing chamber fluidically connected to the inlet and the outlet, co-extruding a single, substantially ring-shaped tubular wall having a wall inner circumference, a wall outer circumference, a proximal end, and a distal end, the wall defining at least three channels including a substantially circular primary channel for conveying a first of the fluids, the primary channel having a primary channel outer circumference defined by the wall inner circumference, a proximal opening, and a distal opening, a substantially circular first secondary channel for conveying a second of the fluids, the first secondary channel entirely disposed between the wall inner circumference and the wall outer circumference and having a proximal opening and a second opening, a substantially circular second secondary channel for conveying a third of the fluids, the second secondary channel entirely disposed between the wall inner circumference and the wall outer circumference and having a proximal opening and a second opening, and connecting the proximal end of the wall to the distal connector to fluidically connect the proximal opening of the primary channel to a first of the supplies to supply the first fluid to the primary channel, fluidically connect the proximal opening of the first secondary channel to a second of the supplies to supply the second fluid to the first secondary channel, and fluidically connect the proximal opening of the second secondary channel to a third of the supplies to supply the third fluid to the second secondary channel, connecting the distal end of the wall to the inlet of the mixing connector to fluidically connect the distal opening of the primary channel to the input of the mixing chamber, fluidically connect the second opening of the first secondary channel to the input of the mixing chamber and fluidically connect the second opening of the second secondary channel to the input of the mixing chamber, and fluidically connecting a vascular access device to the outlet of the mixing chamber for simultaneously supplying the at least three medicinal fluids to a patient, the distal opening of the primary channel, the second opening of the secondary channel, and the second opening of the second secondary channel substantially preventing over-pressurization of the vascular access device.

Other features that are considered as characteristic for the invention are set forth in the appended claims.

Although the invention is illustrated and described herein as embodied in a multi-lumen intravenous extension and method for conveying medicinal fluids, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
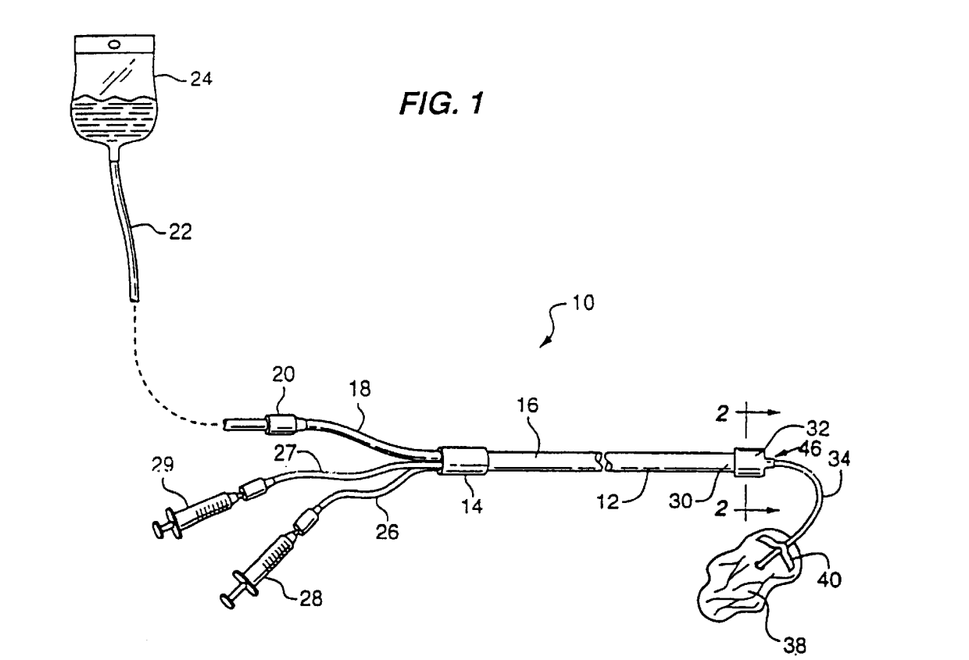
FIG. 1 is a fragmentary, perspective and partially cut-away view of the multi-lumen intravenous extension according to the invention coupled at its input to a bag of saline solution and to two syringes and coupled at its output end to an infusion catheter inserted into a body.

Referring now to the drawings in greater detail, there is illustrated in FIG. 1, an intravenous extension system 10 including a multi-lumen intravenous extension 12 having a connector 14 at the proximal end 16 of the intravenous extension 12. Connected to the proximal end 16 of the intravenous extension 12 is a main infusion conduit or tubing 18 that is connected to a connector 20 that is fluidically connected to tubing 22 extending from a bag 24 of saline solution, for example. Also connected to the connector 14 are first and second tubes 26, 27, which are connected to first and second syringes 28, 29, respectively. It will be understood that each of the syringes 28, 29 can contain a selected drug, medication, or liquid in a predetermined amount that is to be infused into a body 38.

Figure 2:
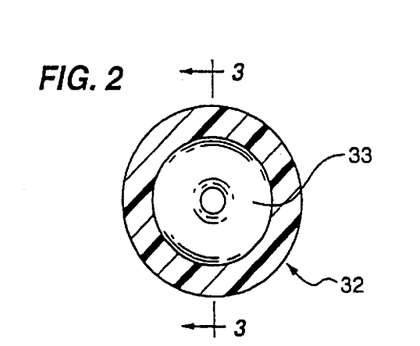
FIG. 2 is a cross-sectional view of a mixing chamber connector or coupling of FIG. 1 along section line 2—2.
Figure 3:
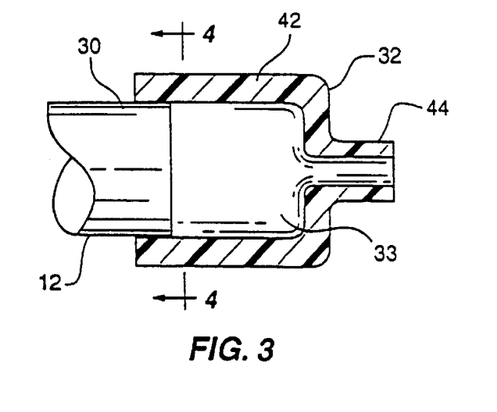
FIG. 3 is a cross-sectional view of the mixing chamber connector or coupling of FIG. 2 along section line 3—3.
Figure 4:
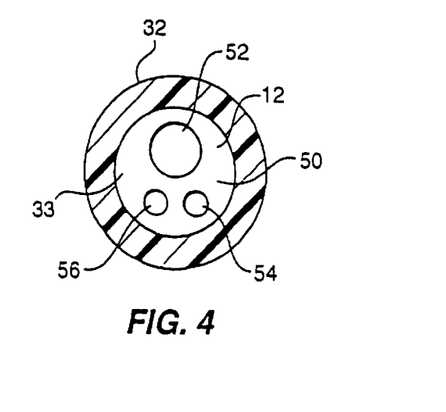
FIG. 4 is a cross-sectional view of the mixing chamber connector or coupling shown in FIG. 3 along line 4—4 with a main lumen and two satellite lumens in the multi-fluid intravenous extension according to the invention.

At a distal end 30 of the multi-lumen intravenous extension 12 is a coupling connector 32 including a mixing chamber 33 (FIGS. 2 to 4). The connector 32 typically can be realized by an industry standard connector, also referred to as a Luer® connector 32. At the outlet of the connector 32 is an infusion needle or intravenous catheter 34, the needle or the catheter being inserted into a body 38 and, typically, held therein by a wing tape or bandage 40.

As best shown in FIGS. 2, 3, and 4, the mixing chamber 33 in the connector 32 has an outer cylindrical wall or tubular portion 42 that is received over the distal end 30 of the multi-lumen intravenous extension 12.

As best shown in FIG. 3, the connector 32 has the larger diameter tubular portion 42 that fits over the distal end 30 of the multi-lumen intravenous extension 12 and a smaller diameter portion 44 at the distal end of the connector 32 that fits over or is connected to a proximal end 46 of the intravenous catheter 34. As such, the connector 32 provides the mixing chamber 33 within the connector 32 where the liquids including a main liquid, such as a saline solution, and one or more medications or drugs or other liquids inserted by the syringe 28 or 29.

When fluid is being introduced into a patient, there is a danger of over-pressurizing the vascular entry point. For example, if a fluid is being injected into a patient's vein too fast, then there exists the possibility of the vein exploding at the vascular access site. The invention substantially prevents such overpressure. Specifically, the distal openings of the lumens 52, 54, 56 at the distal end 30 of the wall open, together, into the mixing chamber 33. Thus, they are fluidically connected to one another through mixing chamber 33. See FIG. 3. If a saline bag is connected to the large lumen 50, for example, the height of the saline bag imparts a fluidic pressure through the vascular access device that is approximately equal to or slightly higher than the internal venous blood pressure of a patient. Such a saline bag is not completely full from the start and begins to empty immediately upon opening the corresponding valve between the bag and the patient. Thus, there is room in the drip chamber and the bag to be filled back up, if necessary.

Because of the fluidic connection between the lumens 52, 54, 56 through the mixing chamber, if a fluid is being injected into any one of the lumens at a pressure higher than the fluidic pressure being exerted inside the mixing chamber, instead of being injected into the patient and causing a possible rupture, the over-pressurized injected fluid actually backs up into the large lumen connected to the saline bag. Accordingly, the invention substantially prevents over-pressurization of the catheter disposed in the patient.

The following examples explain how fluid flows without the extension of the present invention and with the extension of the present invention and, specifically, how the present invention prevents over-pressurization of the venous access site when a bolus of medicinal fluid is introduced at a fast rate into one of its infusion lumens.

Both experimentally and theoretically it can be shown that with a steady, relatively firm force of 9 pounds on the plunger of a common 12 cc syringe (producing 29 PSIG), water-like fluids will flow at a rate of about 1.5 cc/sec through the 1 meter long 0.030 inch (0.76 mm) ID extension 12 of the present invention. (These theoretical calculations apply the Hagen-Poiseuille Law mentioned above.) For simplicity, a constant flow rate of injectate of 1.0 cc/second from a 12 cc syringe into a drug infusion lumen is considered. Using the same theoretical formula, it is possible to calculate a pressure drop of 17.5 PSI from the syringe connector through the infusion lumen to the mixing chamber, which is 1 meter downstream. In contrast, a 20-gauge needle 50 millimeters long commonly used for injecting drugs venously, which has an inner diameter of 0.024 inches (0.60 mm), creates a 2.3 PSI drop in pressure at the same flow rate. In other words, if 17.5 PSI (9 lbs of force) were to be exerted on the plunger of a 12 cc syringe-20 Ga needle assembly without the extension of the present invention, then approximately 15 PSI of fluid pressure would be transferred directly through the needle to the vein, a pressure that is about 200 times normal venous pressure.

If such a typically IV set-up is, then, considered using the extension of the present invention, it is possible to estimate the relative flows and pressures to be expected in such a system when a medicinal fluid is injected through the injection lumen having an ID of 0.030 inches. Typically, IV fluids are delivered from a bag about 3 feet higher than the venous injection site. Such a configuration produces a pressure of approximately 1.5 PSI (Gauge) created by the column of fluid in the tubing at the "mixing chamber" located next to the venous injection site and result in a maximum flow rate into the vein of 0.65 cc/second if no restriction is created by pinching off the tubing as in normal operation (i.e., what is referred to as "wide open operation"). Then, if medicinal fluid is injected in the infusion lumen of the present invention at the rate of 1 cc/second, the pressure at the mixing chamber would be relieved by the shunting of fluid into the main IV lumen, which can only create a back pressure of about 1.5 PSIG (as above). The relative flow rates through the 20 Ga. needle versus the main lumen 52 can be calculated using the Hagen Poiseuille law and yields the ratio of approximately 1 to 40 for any mixing chamber pressure, due mainly to the differences in lumen diameters. In other words, if 1 cc per second of medicinal fluid is forced into the infusion lumen of the present invention while it is attached to an intravenous system, 0.025 cc/sec. of that fluid will flow through the needle and 0.975 cc/sec. will be shunted back into the main IV lumen through the mutually communicating mixing chamber. The only increase in pressure expected in the mixing chamber will, then, be due to the resistance to the flow of 0.975 cc/sec. through 2 meters of the main lumens of both the extension and IV set connected to it. Again, using the fluid flow law as above, an increase in pressure is only 0.1 PSI. When added to the normal 1.5 PSIG of a normally operating IV system, this relatively fast infusion rate creates an increase of pressure of less than 10 percent at the needle entrance. (There is an equivalent small increase of flow through the needle as well). This increase is not considered to be traumatic to the vein and is orders of magnitude smaller than direct infusion through a needle or through the systems described in the prior art documents referenced above.

Figure 5:
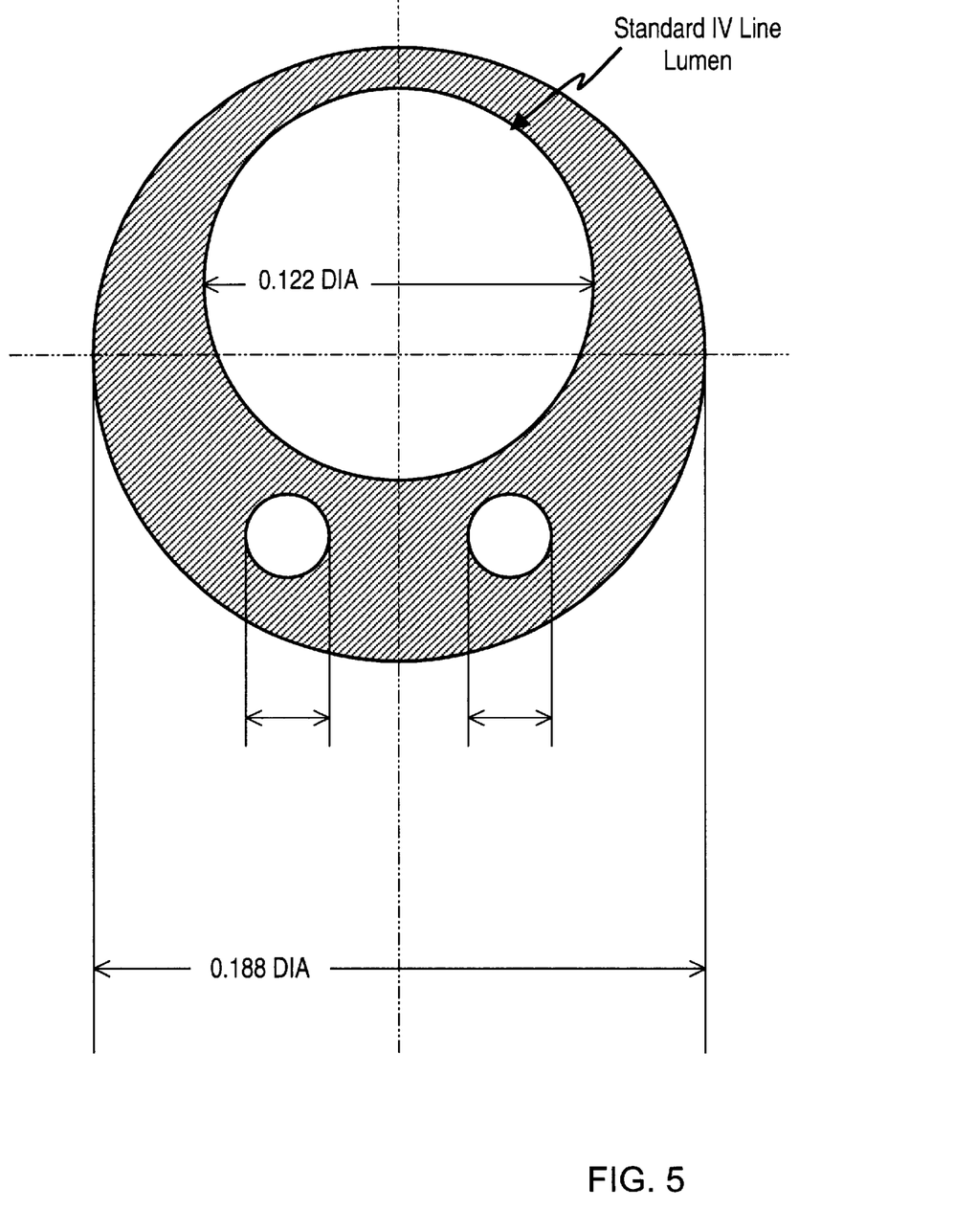
FIG. 5 is a cross-sectional view of the multi-lumen intravenous extension according to the invention with a primary lumen and two secondary lumens.

As best shown in FIG. 4, the multi-lumen intravenous extension 12 has a main cylindrical body portion 50 with a main lumen 52 extending axially therein and two satellite lumens 54 and 56 therein extending parallel to the main lumen 52 in the body 50. FIG. 5 illustrates the preferred embodiment of the multi-lumen intravenous extension 12 according to the invention where the main lumen 52 has a diameter of 0.122" corresponding to a standard IV line lumen and the satellite lumens 54, 56 have a diameter of 0.030". The overall outer diameter of the extension 12 is 0.188".

In a preferred embodiment of the present invention illustrated in FIGS. 4 and 5, the secondary channels, satellite lumens 54, 56, have a diameter of 0.030 to 0.050 inches with no impedance on the primary channel—main lumen 52. Because of the intramural extrusion construction of the present invention, in a standard size tubing having an outer diameter of approximately 0.190 inches, four or even more secondary channels can be co-extruded into the wall of the extension of the present invention without having any impact on the flow through the primary channel, main lumen 52. It is noted that if, for example, one of the 0.030" diameter lumen of the present invention were introduced into the outer tube 52 of Vaillancourt, then flow in the outer tube 52 would decrease by at least 45 percent.

Figure 6:
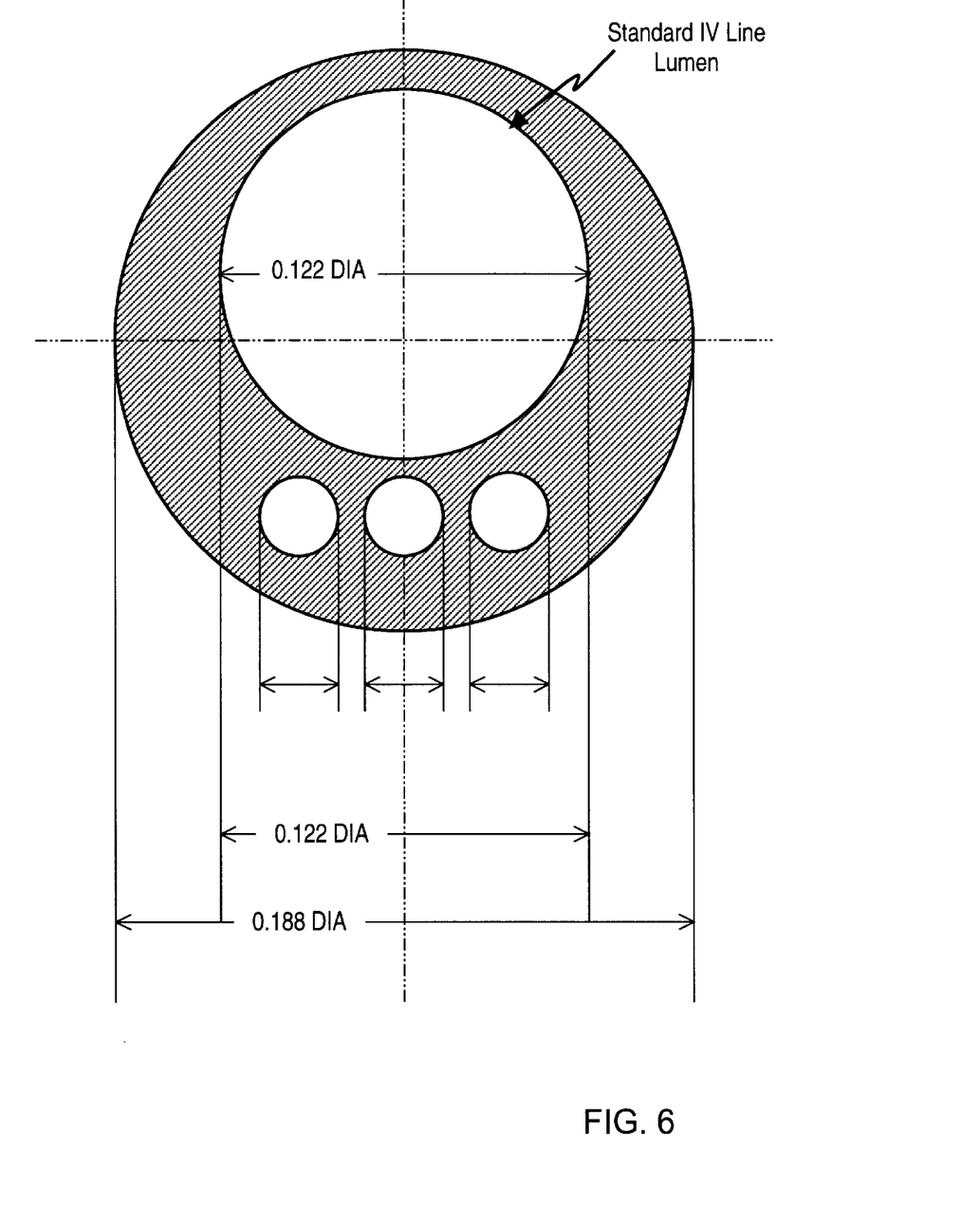
FIG. 6 is a cross-sectional view of the multi-lumen intravenous extension according to the invention with a primary lumen and three secondary lumens.
Figure 7:
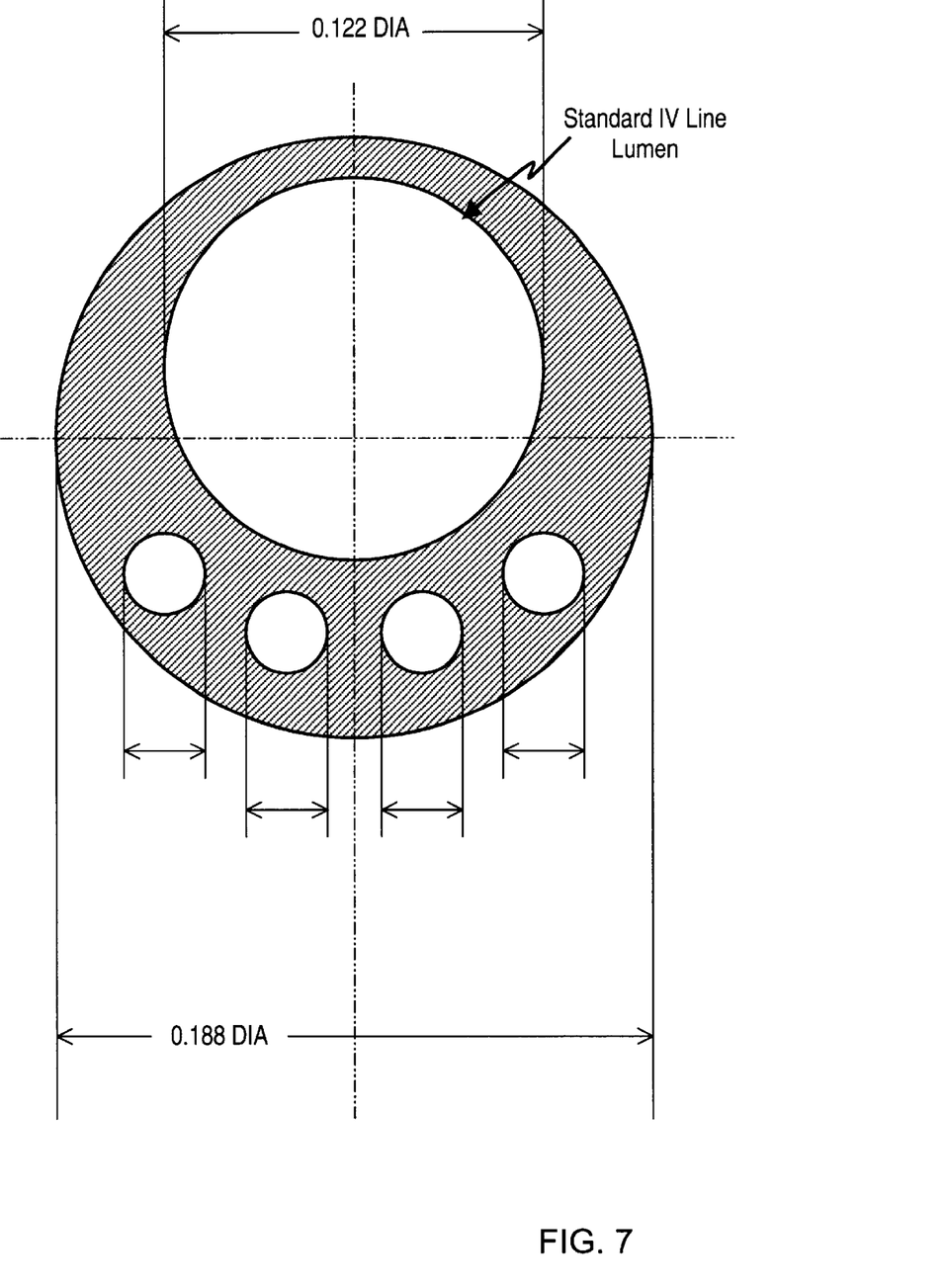
FIG. 7 is a cross-sectional view of the multi-lumen intravenous extension according to the invention with a primary lumen and four secondary lumens.

As shown in FIGS. 6, and 7, there can be three or four satellite lumens 54, 56, 58, 60. As shown in these figures, the three illustrated multi-lumen configurations, and a non-illustrated but similar fourth configuration having five satellite lumens, all can be formed while maintaining the overall outer diameter of the extension 12 at 0.188".

As more than two secondary lumens can exist in the extension 12 of the present invention, more than just the first and second tubes 26, 27 can be connected to more than just the first and second syringes 28, 29 that are illustrated in FIG. 1, each of which, respectively, being able to contain a selected drug, medication, or liquid in a predetermined amount that is to be infused into a body.

It will be understood that the primary lumen 52 has an internal diameter or cross-sectional area approximately that of a standard intravenous infusion system. The primary or main lumen 52 may have variable shapes and septation.

The proximal connector 14 can be of different types of standard female type connectors.

The satellite or secondary lumens 54 and 56 may have variable shapes and septation and cross-sectional areas, and they will extend the majority length of the multi-lumen intravenous extension 12.

The intramural extruded configuration of the present invention entirely eliminates the drawbacks of the prior art because flow in the primary channel, main lumen 52, is entirely unimpeded.

The multi-lumen one-piece extrusion that forms the elongate body of extension 12 is manufactured by extruding pressurized molten plastic (referred to as the "melt") through a die having thin septa supporting metal tubing in its orifice. As the plastic is ejected through the die and pulled through a cooling water trough at constant speeds, air pressure is being introduced into the tubing within the die to effectively "blow" a channel or "lumen" in the extruded tube. This process is referred to as "air mandrel extrusion." The amount of air pressure along with the outer diameter of the metal tube(s) determines the exact lumen diameter desired. A number of tubes and pressures can produce multiple lumens of various sizes in a continuous length of extruded tubing. Typically, a cutoff machine is used to cut pieces to any length as the extruder is running to aid in handling and manufacture of multi-lumen tubing such as used in the present invention.

Because of the intramural extrusion construction of the present invention, in a standard size tubing having an outer diameter of approximately 0.190 inches, four or even more secondary channels can be co-extruded into the wall of the extension of the present invention without having any impact on the flow through the primary channel, main lumen 52.

If four such secondary channels having a diameter of 0.030 inches were introduced into the Vaillancourt embodiment, then flow in the outer tube 52 would decrease by 100 percent. In other words, the present invention can accommodate at least four secondary channels with no decrease in flow in the main lumen 52 while prior art configurations, such as the Vaillancourt outer tube 52, would be entirely obstructed.

In order to more clearly illustrate this difference between the invention of the instant application and the prior art, in particular, Vaillancourt, applicants submits the following examples where:

1) an internal diameter of a primary lumen is 0.100";
2) a radius of the primary lumen is 0.050";
3) a wall thickness of an internal catheter is 0.010";
4) an Effective area is equal to the area of the primary lumen (the area of an internal catheter multiplied by the number of catheters);
5) an Effective radius is equal to the square root of (Effective Area/$\pi$); and
6) an Effective Flow (Q) is equal to Q in residual lumen divided by Q in primary lumen without catheter.

In the first example of Table 1, the catheter size has an internal diameter of 0.020" and an outer diameter of 0.040".

TABLE #1

| # cath | Eff. Rad | % Change | Eff. Q | % Change |
|---|---|---|---|---|
| 1 | 0.046 | −8% | 0.716 | −28.4% |
| 2 | 0.041 | −18% | 0.452 | −54.8% |
| 3 | 0.036 | −28% | 0.269 | −73.1% |
| 4 | 0.030 | −40% | 0.130 | −87.0% |
| 5 | 0.022 | −56% | 0.037 | −96.3% |
| 6 | 0.010 | −80% | 0.002 | −99.8% |

Thus, for two or more catheters inserted into the Vaillancourt device, there is greater than a 54% decrease in flow.

In the second example of Table 2, the catheter size has an internal diameter of 0.030" and an outer diameter of 0.050".

TABLE #2

| # cath | Eff. Rad | % Change | Eff. Q | % Change |
|---|---|---|---|---|
| 1 | 0.043 | −14% | 0.547 | −45.3% |
| 2 | 0.035 | −30% | 0.240 | −76% |
| 3 | 0.025 | −50% | 0.063 | −93.7% |
| 4 | 0.000 | | | OBSTRUCTED |

Thus, for only one catheter inserted in into the Vaillancourt device, there is greater than a 45% decrease in flow. Significantly, the Vaillancourt device cannot accommodate four catheters because it would be entirely obstructed.

In the third example of Table 3, the catheter size has an internal diameter of 0.040" and an outer diameter of 0.060".

TABLE #3

| # cath | Eff. Rad | % Change | Eff. Q | % Change |
|---|---|---|---|---|
| 1 | 0.040 | −20% | 0.410 | −59% |
| 2 | 0.026 | −48% | 0.073 | −92.7% |
| 3 | | Exceeds Area of Primary Lumen | | |

Thus, for only one catheter inserted in into the Vaillancourt device, there is greater than a 59% decrease in flow. Significantly, the Vaillancourt device cannot accommodate even three catheters because the catheters exceed the area of the primary lumen.

Finally, Table 4 provides an example corresponding to the embodiment shown in FIG. 8 of Vaillancourt.

TABLE #4

| # cath | Eff. Rad | % Change | Eff. Q | % Change |
|---|---|---|---|---|
| 1 | 0.047 | −6.0% | 0.781 | −21.9% |
| 2 | 0.044 | −12.0% | 0.600 | −40% |
| 3 | 0.040 | −20% | 0.410 | −59% |
| 4 | 0.036 | −28% | 0.269 | −73.1% |
| 5 | 0.032 | −36% | 0.168 | −83.2% |
| 6 | 0.026 | −48% | 0.073 | −92.7% |

Thus, for at least two catheters inserted in into the Vaillancourt device, there is greater than a 40% decrease in flow.

In significant contrast to the prior art, the present invention allows four or more internal satellite catheters to be extruded in a single extension 12 with absolutely no impact on flow through a main lumen configured according to standard medical IV tubing having a diameter of 0.122".

The configuration according to the present invention allows flow of fluids and medications in the secondary channels with viscosities significantly higher than saline, for example, PROPOFOL®, which uses 5% intralipid as a carrier fluid. More specifically, applicant has been successful in pushing a significantly viscous liquid, such as maple syrup, through one of the secondary channels of the present invention.

The multi-lumen intravenous extension system 10 of the present invention has a number of advantages that result in improved patient safety. A primary advantage is that pharmaceutical agents can be delivered near the intra-vascular site without altering normal fluid dynamics of the infusion system 10. Other advantages of delivery of pharmaceutical agents near the intra-vascular access site include:

infusion of multiple pharmaceutical agents into a single intra-vascular site with minimal mixing of agents;

infusion of liquid agents through the satellite lumens 54 and 56 not being dependent upon carrier fluid rates for delivery;

more rapid onsets of the action of the agents delivered;

delivery of a higher concentration of agents at the infusion site; and alterations of carrier fluid rates having minimal effect upon delivery of the agents infused through the satellite lumens 54 and 56.

Still another advantage of the multi-lumen intravenous extension system of the present invention is related to the infusion of agents through small volume secondary channels, i.e., the smaller-in-diameter satellite or secondary lumens 54 and 56. Some of these advantages include:

decreased priming volume by reducing "tubing dead space";

independent infusion of multiple agents;

reduction in carrier fluid rate requirements; and simplified and efficient access to the intra-vascular infusion site.

The multi-lumen intravenous extension system of the present invention should decrease the confusion frequently associated with multiple access port infusion systems that is sometimes incurred with the systems disclosed in Thomsen (U.S. Pat. No. 4,908,018) and Oswald et al. (U.S. Pat. No. 5,190,525). Further, the multi-lumen intravenous extension system will very likely improve the response time for the onset of the action desired in the patient from the infused agents a result of the fact that the injection site of the infused agent (the "mixing chamber") is adjacent to the venous access site in the present invention. In contrast, a common intravenous infusion set injection port (also known as a "Y" connector) is typically one half meter or more from the venous access site. This difference is substantial in that, in the present invention, a bolus of agent(s) immediately introduced, whereas, in a Y-connector, a bolus of agent must travel though a minimum of one half of a meter before it reaches the patient's vein. That half meter of IV tubing contains approximately 4 cc of normally supplied IV fluid, which would have to be injected immediately in front of the bolus with the tubing occluded from above, causing venous overpressure. Alternatively, the bolus would have to travel slowly through a normal drip flow rate, resulting in potentially damaging delays in emergent situations as well as some dilution. Thus, injecting through the present invention will improve the response time for the drug infused.

Finally, the low priming volume and reduction in carrier fluid rate requirements reduces the potential for fluid overload in volume sensitive patients.

The multi-lumen intravenous extension system 10 of the present invention can be used in a number of critical applications. For example, it can be used in anesthesia during operations for infusion of anesthetic agents, vasoactive agents, antibiotics, and antiarrhymics. It can be used with a PCA pump. It can be used, in ICU for vaso-active meds, antiarrhymics, potassium, antibiotics, insulin, etc. It can be used for pediatric anesthesia, namely, for supplying the appropriate pharmaceutical agents. It also can be used in neonatal and pediatric ICU.

From the foregoing description, it will be appreciated that the multi-lumen intravenous extension system 10 of the present invention including the multi-lumen intravenous extension 12 and the mixing chamber 33 in the connector 32 provide a number of advantages, some of which have been described above and others of which are inherent in the invention.

I claim:

1. In a drug delivery system having a medicinal fluid supply system with at least two supplies independently supplying at least two medicinal fluids at a distal connector, an extension comprising:

a mixing connector defining a mixing chamber to be fluidically connected to a vascular access device for simultaneously supplying the at least two medicinal fluids to a patient, said mixing connector being a male Luer lock connector and having a size equal to the medical industry standard for insertion into the vascular access device; and an intramural extrusion tube for conveying the at least two medicinal fluids independent from one another, said tube having:

a proximal end capable of being connected to the distal connector;

a distal end connected to the mixing connector;
a single, substantially ring-shaped tubular wall having:
   a wall inner circumference; and
   a wall outer circumference;
said wall defining at least two channels including:
   a substantially circular primary channel for conveying a first of the medicinal fluids, said primary channel having:
      a primary channel outer circumference defined by said wall inner circumference;
      a proximal opening capable of being fluidically connected to a first of the supplies to supply the first medicinal fluid to said primary channel; and
      a distal opening fluidically connected to said mixing chamber for substantially preventing over-pressurization of the vascular access device; and
   a substantially circular secondary channel for conveying a second of the medicinal fluids, said secondary channel entirely disposed between said wall inner circumference and said wall outer circumference and having:
      a proximal opening capable of being fluidically connected to a second of the supplies to supply the second medicinal fluid to said secondary channel; and
      a distal opening fluidically connected to said mixing chamber for substantially preventing over-pressurization of the vascular access device.

2. The extension according to claim 1, wherein said vascular access device is a catheter.

3. The extension according to claim 1, wherein:
said intramural extrusion tube conveys at least three medicinal fluids independent from one another;
said wall defines at least three channels including a substantially circular second secondary channel for conveying a third of the medicinal fluids; and
said second secondary channel is entirely disposed between said wall inner circumference and said wall outer circumference and has:
   a proximal opening capable of being fluidically connected to a third of the supplies to supply the third medicinal fluid to said second secondary channel; and
   a distal opening fluidically connected to said mixing chamber.

4. A drug delivery system, comprising:
a medicinal fluid supply system having a distal connector and at least two supplies independently supplying at least two medicinal fluids at said distal connector;
a mixing connector defining a mixing chamber;
an intramural extrusion tube for conveying the at least two medicinal fluids independent from one another, said tube having:
   a proximal end connected to said distal connector;
   a distal end connected to said mixing connector;
   a single, substantially ring-shaped tubular wall having:
      a wall inner circumference; and
      a wall outer circumference;
   said wall defining at least two channels including:
      a substantially circular primary channel for conveying a first of the medicinal fluids, said primary channel having:
         a primary channel outer circumference defined by said wall inner circumference;
         a proximal opening fluidically connected to a first of said supplies to supply the first medicinal fluid to said primary channel; and
         a distal opening fluidically connected to said mixing chamber;
      a substantially circular secondary channel for conveying a second of the medicinal fluids, said secondary channel entirely disposed between said wall inner circumference and said wall outer circumference and having:
         a proximal opening fluidically connected to a second of said supplies to supply the second medicinal fluid to said secondary channel; and
         a distal opening fluidically connected to said mixing chamber; and
a vascular access device fluidically connected to said mixing chamber for simultaneously supplying the at least two medicinal fluids to a patient, said distal opening of said primary channel and said distal opening of said secondary channel substantially preventing over-pressurization of said vascular access device.

5. The system according to claim 4, wherein said mixing connector is a male Luer lock connector.

6. The system according to claim 5, wherein said mixing connector has a size equal to the medical industry standard for insertion into a vascular access device.

7. The system according to claim 4, wherein said vascular access device is a catheter.

8. The system according to claim 4, wherein:
said intramural extrusion tube conveys at least three medicinal fluids independent from one another;
said wall defines at least three channels including a substantially circular second secondary channel for conveying a third of the medicinal fluids; and
said second secondary channel is entirely disposed between said wall inner circumference and said wall outer circumference and has:
   a proximal opening fluidically connected to a third of said supplies to supply the third medicinal fluid to said second secondary channel; and
   a distal opening fluidically connected to said mixing chamber for substantially preventing over-pressurization of said vascular access device.

9. In combination with a drug delivery system having:
a medicinal fluid supply system having a distal connector and at least two supplies independently supplying at least two medicinal fluids at the distal connector;
a mixing connector defining a mixing chamber; and
a vascular access device fluidically connected to the mixing chamber for simultaneously supplying the at least two medicinal fluids to a patient,
an extension comprising:
   an intramural extrusion tube for conveying the at least two medicinal fluids independent from one another, said tube having:
      a proximal end connected to the distal connector;
      a distal end connected to the mixing connector;
      a single, substantially ring-shaped tubular wall having:
         a wall inner circumference; and
         a wall outer circumference;
      said wall defining at least two channels including:
         a substantially circular primary channel for conveying a first of the medicinal fluids, said primary channel having:
            a primary channel outer circumference defined by said wall inner circumference;

a proximal opening fluidically connected to a first of the supplies to supply the first medicinal fluid to said primary channel; and a distal opening fluidically connected to the mixing chamber for substantially preventing over-pressurization of said vascular access device; and a substantially circular secondary channel for conveying a second of the medicinal fluids, said secondary channel entirely disposed between said wall inner circumference and said wall outer circumference and having:

a proximal opening fluidically connected to a second of the supplies to supply the second medicinal fluid to said secondary channel; and a distal opening fluidically connected to the mixing chamber for substantially preventing over-pressurization of said vascular access device.

10. The extension according to claim 9, wherein the mixing connector is a male Luer lock connector.

11. The extension according to claim 10, wherein the mixing connector has a size equal to the medical industry standard for insertion into a vascular access device.

12. The extension according to claim 9, wherein said vascular access device is a catheter.

13. The extension according to claim 9, wherein:

said intramural extrusion tube conveys at least three medicinal fluids independent from one another;

said wall defines at least three channels including a substantially circular second secondary channel for conveying a third of the medicinal fluids; and said second secondary channel is entirely disposed between said wall inner circumference and said wall outer circumference and has:

a proximal opening fluidically connected to a third of the supplies to supply the third medicinal fluid to said second secondary channel; and a distal opening fluidically connected to the mixing chamber for substantially preventing over-pressurization of the vascular access device.

14. A drug delivery extension, comprising:

a mixing connector defining a mixing chamber to be fluidically connected to a vascular access device for simultaneously supplying at least four medicinal fluids to a patient; and an intramural extrusion tube for conveying the at least four medicinal fluids independent from one another, said tube having:

a proximal end;

a distal end;

a single, substantially ring-shaped tubular wall having:
a wall inner circumference; and
a wall outer circumference;

said wall defining at least four channels including:

a substantially circular primary channel for conveying a first fluid, said primary channel having:
a primary channel outer circumference defined by said wall inner circumference; and
first and second openings respectively opening at said proximal end and said distal end;

a substantially circular first secondary channel for conveying a second fluid, said first secondary channel entirely disposed between said wall inner circumference and said wall outer circumference and having first and second openings respectively opening at said proximal end and said distal end;

a substantially circular second secondary channel for conveying a third fluid, said second secondary channel entirely disposed between said wall inner circumference and said wall outer circumference and having first and second openings respectively opening at said proximal end and said distal end; and a substantially circular third secondary channel for conveying a fourth fluid, said third secondary channel entirely disposed between said wall inner circumference and said wall outer circumference and having first and second openings respectively opening at said proximal end and said distal end, said second opening of said primary channel, said second opening of said first secondary channel, said second opening of said second secondary channel, and said second opening of said third secondary channel, fluidically connected to said mixing chamber and substantially preventing over-pressurization of the vascular access device.

15. The extension according to claim 14, wherein:

said first secondary channel has an outer circumference;

said second secondary channel has an outer circumference; and said primary channel outer circumference is entirely outside said outer circumferences of said first and second secondary channels.

16. The extension according to claim 14, wherein:

said first secondary channel has an outer circumference;

said second secondary channel has an outer circumference; and each of said primary channel outer circumference, said outer circumference of said secondary channel, and said outer circumferences of second secondary channel are entirely separate from one another.

17. The extension according to claim 14, wherein at least one of:

said first opening at said proximal end of said primary channel is to be fluidically connected to a bag of saline;

said first opening at said proximal end of said first secondary channel is to be fluidically connected to a syringe; and said first opening at said proximal end of said second secondary channel is to be fluidically connected to a syringe.

18. The extension according to claim 14, wherein:

said first opening at said proximal end of said first secondary channel is to be fluidically connected to a first syringe;

said first opening at said proximal end of said second secondary channel is to be fluidically connected to a second syringe; and said first opening at said proximal end of said primary channel is to be fluidically connected to a bag of saline.

19. The extension according to claim 14, wherein said primary channel has an internal diameter at least as large as the medical industry standard for infusion tubing.

20. The extension according to claim 14, wherein said primary channel has an internal diameter of approximately 0.122 inches.

21. The extension according to claim 14, wherein:

said primary channel has an internal diameter; and said first secondary channel has no decreasing effect on said internal diameter of said primary channel.

22. The extension according to claim 14, wherein:
said primary channel has an internal diameter; and
each of said first secondary channel and said second secondary channel have no decreasing effect on said internal diameter of said primary channel.

23. The extension according to claim 14, wherein:
said tube has a length; and
said primary channel, said first secondary channel, said second secondary channel, and said third secondary channel each extend through an entirety of said length.

24. The extension according to claim 14, wherein:
said tube has a length; and
said primary channel, said first secondary channel, and second secondary channel each extend through an entirety of said length.

25. The extension according to claim 14, wherein each of said first secondary channel and said second secondary channel has an internal diameter between 0.030 and 0.050 inches.

26. The extension according to claim 14, wherein:
each of said first secondary channel, said second secondary channel, and said third secondary channel has an internal diameter between 0.030 and 0.050 inches.

27. The extension according to claim 14, wherein:
said wall defines a substantially circular fourth secondary channel for conveying a fifth fluid; and
said fourth secondary channel is entirely disposed between said wall inner circumference and said wall outer circumference and has first and second openings respectively opening at said proximal end and said distal end, said second opening of said fourth secondary channel is fluidically connected to said mixing chamber and substantially prevents over-pressurization of said vascular access device.

28. The extension according to claim 27, wherein:
said wall defines a substantially circular fifth secondary channel for conveying a sixth fluid; and
said fifth secondary channel is entirely disposed between said wall inner circumference and said wall outer circumference and has first and second openings respectively opening at said proximal end and said distal end, said second opening of said fifth secondary channel is fluidically connected to said mixing chamber and substantially prevents over-pressurization of said vascular access device.

29. A method for conveying at least four medicinal fluids independent from one another, which comprises:
providing a mixing connector defining a mixing chamber to be fluidically connected to a vascular access device for simultaneously supplying the at least four medicinal fluids to a patient;
co-extruding a single, substantially ring-shaped tubular wall having a wall inner circumference, a wall outer circumference, a proximal end, and a distal end, the wall defining at least two channels including:
a substantially circular primary channel for conveying a first of the fluids, the primary channel having:
a primary channel outer circumference defined by the wall inner circumference; and
first and second openings respectively opening at the proximal end and the distal end; and
a substantially circular first secondary channel for conveying a second of the fluids, the first secondary channel being entirely disposed between the wall inner circumference and the wall outer circumference and having first and second openings respectively opening at the proximal end and the distal end;
a substantially circular second secondary channel for conveying a third of the fluids, the second secondary channel being entirely disposed between the wall inner circumference and the wall outer circumference and having first and second openings respectively opening at the proximal end and the distal end;
a substantially circular third secondary channel for conveying a fourth of the fluids, the third secondary channel being entirely disposed between the wall inner circumference and the wall outer circumference and having first and second openings respectively opening at the proximal end and the distal end; and
fluidically connecting the second opening of the primary channel, the second opening of the first secondary channel, the second opening of the second secondary channel, and the second opening of the third secondary channel to said mixing chamber and, thereby, substantially prevent over-pressurization of the vascular access device.

30. A method for delivering at least two medicinal fluids, which comprises:
providing a medicinal fluid supply system having a distal connector and at least two supplies independently supplying at least two medicinal fluids at the distal connector;
providing a mixing connector having an inlet and an outlet and defining a mixing chamber fluidically connected to the inlet and the outlet;
co-extruding a single, substantially ring-shaped tubular wall having a wall inner circumference, a wall outer circumference, a proximal end, and a distal end, the wall defining at least two channels including:
a substantially circular primary channel for conveying a first of the fluids, the primary channel having:
a primary channel outer circumference defined by the wall inner circumference;
a proximal opening; and
a distal opening;
a substantially circular secondary channel for conveying a second of the fluids, the secondary channel entirely disposed between the wall inner circumference and the wall outer circumference and having:
a proximal opening; and
a second opening; and
connecting the proximal end of the wall to the distal connector to:
fluidically connect the proximal opening of the primary channel to a first of the supplies to supply the first fluid to the primary channel; and
fluidically connect the proximal opening of the secondary channel to a second of the supplies to supply the second fluid to the secondary channel;
connecting the distal end of the wall to the inlet of the mixing connector to:
fluidically connect the distal opening of the primary channel to the input of the mixing chamber;
fluidically connect the second opening of the secondary channel to the input of the mixing chamber; and
fluidically connecting a vascular access device to the outlet of the mixing chamber for simultaneously supplying the at least two medicinal fluids to a patient, the distal opening of the primary channel and the second opening of the secondary channel substantially preventing over-pressurization of the vascular access device.

31. A method for delivering at least three medicinal fluids, which comprises:

provding a medicinal fluid supply system having a distal connector and at least three supplies independently supplying at least three medicinal fluids at the distal connector;

providing a mixing connector having an inlet and an outlet and defining a mixing chamber fluidically connected to the inlet and the outlet;

co-extruding a single, substantially ring-shaped tubular wall having a wall inner circumference, a wall outer circumference, a proximal end, and a distal end, the wall defining at least three channels including:
- a substantially circular primary channel for conveying a first of the fluids, the primary channel having:
  - a primary channel outer circumference defined by the wall inner circumference;
  - a proximal opening; and
  - a distal opening;
- a substantially circular first secondary channel for conveying a second of the fluids, the first secondary channel entirely disposed between the wall inner circumference and the wall outer circumference and having:
  - a proximal opening; and
  - a second opening;
- a substantially circular second secondary channel for conveying a third of the fluids, the second secondary channel entirely disposed between the wall inner circumference and the wall outer circumference and having:
  - a proximal opening; and
  - a second opening; and connecting the proximal end of the wall to the distal connector to:
- fluidically connect the proximal opening of the primary channel to a first of the supplies to supply the first fluid to the primary channel;
- fluidically connect the proximal opening of the first secondary channel to a second of the supplies to supply the second fluid to the first secondary channel; and
- fluidically connect the proximal opening of the second secondary channel to a third of the supplies to supply the third fluid to the second secondary channel;

connecting the distal end of the wall to the inlet of the mixing connector to:
- fluidically connect the distal opening of the primary channel to the input of the mixing chamber;
- fluidically connect the second opening of the first secondary channel to the input of the mixing chamber; and
- fluidically connect the second opening of the second secondary channel to the input of the mixing chamber; and fluidically connecting a vascular access device to the outlet of the mixing chamber for simultaneously supplying the at least three medicinal fluids to a patient, the distal opening of the primary channel, the second opening of the secondary channel, and the second opening of the second secondary channel substantially preventing over-pressurization of the vascular access device.

* * * * *